United States Patent
Holakovsky et al.

(10) Patent No.: US 9,757,750 B2
(45) Date of Patent: Sep. 12, 2017

(54) MEDICINAL DEVICE WITH CONTAINER

(75) Inventors: Holger Holakovsky, Witten (DE); Lars Lange, Ratingen (DE); Maurice Steinzen, Selm (DE); Felix Weiland, Guetersloh (DE); Klaus List, Reichelsheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 734 days.

(21) Appl. No.: 13/434,950

(22) Filed: Mar. 30, 2012

(65) Prior Publication Data

US 2012/0325204 A1 Dec. 27, 2012

(30) Foreign Application Priority Data

Apr. 1, 2011 (EP) .................... 11160773

(51) Int. Cl.
*B05B 11/00* (2006.01)
*A61M 15/00* (2006.01)

(52) U.S. Cl.
CPC ..... *B05B 11/0013* (2013.01); *A61M 15/0026* (2014.02); *A61M 15/0036* (2014.02); *A61M 15/0065* (2013.01); *B05B 11/0043* (2013.01); *B05B 11/0054* (2013.01); *B05B 11/3091* (2013.01)

(58) Field of Classification Search
CPC .......... A61M 15/0026; A61M 15/0036; A61M 15/0065; B05B 11/0013; B05B 11/0043; B05B 11/0054
USPC .................... 128/200.23; 222/92, 93, 95, 105
See application file for complete search history.

(56) References Cited

U.S. PATENT DOCUMENTS

| | | | |
|---|---|---|---|
| 1,828,864 A | 10/1931 | Hopkins |
| 2,015,970 A | 10/1935 | Schoene |
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |

(Continued)

FOREIGN PATENT DOCUMENTS

| | | |
|---|---|---|
| AU | 2005201364 A1 | 7/2006 |
| CA | 1094549 A | 1/1981 |

(Continued)

OTHER PUBLICATIONS

International Search Report for PCT/EP2012/055209 mailed Jan. 6, 2012.

(Continued)

*Primary Examiner* — Justine Yu
*Assistant Examiner* — Kathrynn Lyddane
(74) *Attorney, Agent, or Firm* — Paula K. Wittmayer; Philip I. Datlow

(57) ABSTRACT

The invention relates to a hand-held medicinal device, particularly a nebulizer, for delivering a liquid medicament preparation from a container having a container cap. The medicament preparation may be based for example on an alcoholic solvent or may contain a similar substance with an increased vapor pressure. The proposed nebulizer with the installed container comprises a sealing system made up of two seals at the junction between the device and container, which prevent loss of liquid, diffusion leaks and exchange of gases with the environment at this point.

15 Claims, 9 Drawing Sheets

(56) References Cited

U.S. PATENT DOCUMENTS

| | | |
|---|---|---|
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,354,883 A | 11/1967 | Southerland |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,802,604 A | 4/1974 | Morane et al. |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,456,016 A | 6/1984 | Nowacki et al. |
| 4,467,965 A | 8/1984 | Skinner |
| 4,476,116 A | 10/1984 | Anik |
| 4,515,586 A | 5/1985 | Mendenhall et al. |
| 4,516,967 A | 5/1985 | Kopfer |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,444 E | 11/1990 | Lerner |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A * | 12/1996 | Kohler .................... 128/203.15 |
| 5,593,069 A | 1/1997 | Jinks |
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A * | 7/1998 | Alband .................... 128/200.23 |
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley et al. |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |
| 5,950,016 A | 9/1999 | Tanaka |

(56) References Cited

U.S. PATENT DOCUMENTS

| | | |
|---|---|---|
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cirrillo et al. |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 * | 8/2001 | de Pous .............. B05B 11/0013 222/321.9 |
| 6,302,101 B1 | 10/2001 | Py |
| 6,315,173 B1 | 11/2001 | Di Giovanni et al. |
| 6,319,943 B1 | 11/2001 | Joshi et al. |
| 6,341,718 B1 | 1/2002 | Schilthuizen et al. |
| 6,349,856 B1 * | 2/2002 | Chastel ............... B05B 11/3047 222/321.7 |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | van der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 * | 2/2004 | Freund et al. ................ 604/403 |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,167,171 B2 | 5/2012 | Moretti |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,950,393 B2 | 2/2015 | Holakovsky et al. |
| 8,960,188 B2 | 2/2015 | Bach et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0007155 A1 | 1/2002 | Freund et al. |
| 2002/0046751 A1 | 4/2002 | MacRae et al. |

(56) References Cited

U.S. PATENT DOCUMENTS

| | | |
|---|---|---|
| 2002/0060255 A1 | 5/2002 | Benoist |
| 2002/0074429 A1 | 6/2002 | Hettrich et al. |
| 2002/0079285 A1 | 6/2002 | Jansen |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0085254 A1 | 5/2003 | Katooka et al. |
| 2003/0098023 A1 | 5/2003 | Drachmann et al. |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 | 5/2004 | Schyra et al. |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0231667 A1 | 11/2004 | Horton et al. |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239930 A1 | 10/2006 | Lamche et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1 | 3/2007 | Geser et al. |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1 | 7/2007 | Rohrschneider et al. |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0272763 A1 | 11/2007 | Dunne et al. |
| 2007/0298116 A1 | 12/2007 | Bechtold-Peters et al. |
| 2008/0017192 A1 | 1/2008 | Southby et al. |
| 2008/0029085 A1 | 2/2008 | Lawrence et al. |
| 2008/0083408 A1 | 4/2008 | Hodson et al. |
| 2008/0092885 A1 | 4/2008 | von Schuckmann |
| 2008/0197045 A1 | 8/2008 | Metzger et al. |
| 2008/0249459 A1 | 10/2008 | Godfrey et al. |
| 2008/0265198 A1 | 10/2008 | Warby |
| 2008/0283553 A1 | 11/2008 | Cox et al. |
| 2008/0308580 A1 | 12/2008 | Gaydos et al. |
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0221626 A1 | 9/2009 | Schmidt |
| 2009/0235924 A1 | 9/2009 | Holakovsky et al. |
| 2009/0272664 A1 | 11/2009 | Marshall et al. |
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |
| 2009/0317337 A1 | 12/2009 | Schmidt |
| 2010/0018524 A1* | 1/2010 | Jinks et al. ............. 128/200.23 |
| 2010/0018997 A1 | 1/2010 | Faneca Llesera |
| 2010/0044393 A1* | 2/2010 | Moretti ............... B05B 11/0043 222/95 |
| 2010/0056559 A1 | 3/2010 | Schmelzer et al. |
| 2010/0084531 A1 | 4/2010 | Schuchman |
| 2010/0095957 A1 | 4/2010 | Corbacho |
| 2010/0144784 A1 | 6/2010 | Schmelzer et al. |
| 2010/0168710 A1 | 7/2010 | Braithwaite |
| 2010/0237102 A1 | 9/2010 | Margheritis |
| 2010/0242557 A1 | 9/2010 | Spreitzer et al. |
| 2010/0242954 A1 | 9/2010 | Hahn et al. |
| 2011/0005517 A1 | 1/2011 | Boeck et al. |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |

(56) References Cited

U.S. PATENT DOCUMENTS

| | | |
|---|---|---|
| 2015/0040890 A1 | 2/2015 | Besseler et al. |
| 2015/0040893 A1 | 2/2015 | Besseler et al. |
| 2015/0041558 A1 | 2/2015 | Besseler et al. |
| 2015/0114387 A1 | 4/2015 | Bach et al. |
| 2015/0122247 A1 | 5/2015 | Besseler et al. |
| 2015/0258021 A1 | 9/2015 | Kreher et al. |
| 2015/0306087 A1 | 10/2015 | Schmelzer et al. |
| 2015/0320947 A1 | 11/2015 | Eicher et al. |
| 2015/0320948 A1 | 11/2015 | Eicher et al. |
| 2016/0095992 A1 | 4/2016 | Wachtel |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0289336 A2 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0778221 A1 | 6/1997 |
| EP | 0845253 A2 | 6/1998 |
| EP | 0845265 A1 | 6/1998 |
| EP | 0860210 A2 | 8/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 A1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |
| GB | 1524431 A | 9/1978 |
| GB | 2081396 A | 2/1982 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | 06312019 A | 11/1994 |
| JP | H07118164 A | 5/1995 |
| JP | H07118166 A | 5/1995 |
| JP | 07323086 A | 12/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2003511212 A | 3/2003 |
| JP | 2003299717 A | 10/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |
| JP | 2010526620 A | 8/2010 |
| JP | 2010540371 A | 12/2010 |
| WO | 8100674 A1 | 3/1981 |
| WO | 8200785 A1 | 3/1982 |
| WO | 8300288 A1 | 2/1983 |
| WO | 8303054 A1 | 9/1983 |
| WO | 8605419 A1 | 9/1986 |
| WO | 8706137 A1 | 10/1987 |
| WO | 8803419 A1 | 5/1988 |
| WO | 8900889 A1 | 2/1989 |
| WO | 8900947 A1 | 2/1989 |
| WO | 8902279 A1 | 3/1989 |
| WO | 8903672 A1 | 5/1989 |
| WO | 8903673 A1 | 5/1989 |
| WO | 8905139 A1 | 6/1989 |
| WO | 9009780 A1 | 9/1990 |
| WO | 9009781 A1 | 9/1990 |
| WO | 9114468 A1 | 10/1991 |
| WO | 9206704 A1 | 4/1992 |
| WO | 9217231 A1 | 10/1992 |
| WO | 9221332 A1 | 12/1992 |
| WO | 9222286 | 12/1992 |
| WO | 9313737 A1 | 7/1993 |
| WO | 9324164 A1 | 12/1993 |
| WO | 9325321 A1 | 12/1993 |
| WO | 9407607 A1 | 4/1994 |
| WO | 9417822 A1 | 8/1994 |

(56) References Cited

FOREIGN PATENT DOCUMENTS

| | | |
|---|---|---|
| WO | 9425371 A1 | 11/1994 |
| WO | 9427653 A2 | 12/1994 |
| WO | 9503034 A1 | 2/1995 |
| WO | 9532015 A1 | 11/1995 |
| WO | 9600050 A1 | 1/1996 |
| WO | 9606011 A2 | 2/1996 |
| WO | 9606581 A1 | 3/1996 |
| WO | 9623522 A1 | 8/1996 |
| WO | 9701329 A1 | 1/1997 |
| WO | 9706813 A1 | 2/1997 |
| WO | 9706842 A1 | 2/1997 |
| WO | 9712683 A1 | 4/1997 |
| WO | 9712687 A1 | 4/1997 |
| WO | 9720590 A1 | 6/1997 |
| WO | 9723208 A1 | 7/1997 |
| WO | 9727804 A1 | 8/1997 |
| WO | 9735562 A1 | 10/1997 |
| WO | 9741833 A1 | 11/1997 |
| WO | 9812511 A2 | 3/1998 |
| WO | 9827959 A2 | 7/1998 |
| WO | 9831346 A1 | 7/1998 |
| WO | 9839043 A1 | 9/1998 |
| WO | 9901227 A1 | 1/1999 |
| WO | 9907340 A1 | 2/1999 |
| WO | 9911563 A1 | 3/1999 |
| WO | 9916530 A1 | 4/1999 |
| WO | 9943571 A1 | 9/1999 |
| WO | 9962495 A2 | 12/1999 |
| WO | 9965464 | 12/1999 |
| WO | 0001612 A2 | 1/2000 |
| WO | 0023037 A1 | 4/2000 |
| WO | 0023065 A2 | 4/2000 |
| WO | 0027543 A1 | 5/2000 |
| WO | 0033965 A1 | 6/2000 |
| WO | 0037336 A1 | 6/2000 |
| WO | 0049988 A2 | 8/2000 |
| WO | 0064779 A1 | 11/2000 |
| WO | 0113885 A1 | 3/2001 |
| WO | 0128489 A1 | 4/2001 |
| WO | 0164182 A2 | 9/2001 |
| WO | 0185097 A2 | 11/2001 |
| WO | 0187392 A2 | 11/2001 |
| WO | 0197888 A2 | 12/2001 |
| WO | 0198175 A1 | 12/2001 |
| WO | 0198176 A2 | 12/2001 |
| WO | 0204054 A1 | 1/2002 |
| WO | 0205879 A1 | 1/2002 |
| WO | 0217988 A2 | 3/2002 |
| WO | 0232899 A1 | 4/2002 |
| WO | 0234411 A1 | 5/2002 |
| WO | 02070141 A1 | 9/2002 |
| WO | 02089887 A1 | 11/2002 |
| WO | 03002045 A1 | 1/2003 |
| WO | 03014832 A1 | 2/2003 |
| WO | 03020253 A2 | 3/2003 |
| WO | 03022332 A2 | 3/2003 |
| WO | 03035030 A1 | 5/2003 |
| WO | 03037159 A2 | 5/2003 |
| WO | 03037259 A2 | 5/2003 |
| WO | 03049786 A2 | 6/2003 |
| WO | 03050031 A1 | 6/2003 |
| WO | 03053350 A2 | 7/2003 |
| WO | 03057593 A1 | 7/2003 |
| WO | 03059547 A1 | 7/2003 |
| WO | 03068299 A1 | 8/2003 |
| WO | 03087097 A1 | 10/2003 |
| WO | 03097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 2004033954 A2 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007049239 A2 | 5/2007 |
| WO | 2007060104 A2 | 5/2007 |
| WO | 2007060105 A1 | 5/2007 |
| WO | 2007060106 A1 | 5/2007 |
| WO | 2007060107 A1 | 5/2007 |
| WO | 2007060108 A2 | 5/2007 |
| WO | 2007062721 A1 | 6/2007 |
| WO | 2007090822 A2 | 8/2007 |
| WO | 2007101557 A2 | 9/2007 |
| WO | 2007128381 A1 | 11/2007 |
| WO | 2007134965 A1 | 11/2007 |
| WO | 2007134966 A1 | 11/2007 |
| WO | 2007134967 A1 | 11/2007 |
| WO | 2007134968 A2 | 11/2007 |
| WO | 2007141201 A1 | 12/2007 |
| WO | 2007141203 A1 | 12/2007 |
| WO | 2008023017 A2 | 2/2008 |
| WO | 2008047035 A2 | 4/2008 |
| WO | 2008077623 A1 | 7/2008 |
| WO | 2008124666 A2 | 10/2008 |
| WO | 2008138936 A2 | 11/2008 |
| WO | 2008146025 A2 | 12/2008 |
| WO | 2009006137 A1 | 1/2009 |
| WO | 2009047021 A1 | 4/2009 |
| WO | 2009047173 A2 | 4/2009 |
| WO | 2009050978 A1 | 4/2009 |
| WO | 2009090245 A1 | 7/2009 |
| WO | 2009103510 A1 | 8/2009 |
| WO | 2009115200 A1 | 9/2009 |
| WO | 2010005946 A2 | 1/2010 |
| WO | 2010006870 A1 | 1/2010 |
| WO | 2010094305 A1 | 8/2010 |
| WO | 2010094413 A2 | 8/2010 |
| WO | 2010112358 A2 | 10/2010 |
| WO | 2010133294 A2 | 11/2010 |
| WO | 2011006711 A1 | 1/2011 |
| WO | 2011064160 A1 | 6/2011 |
| WO | 2011064163 A1 | 6/2011 |
| WO | 2011064164 A1 | 6/2011 |
| WO | 2011131779 A1 | 10/2011 |
| WO | 2011154295 A1 | 12/2011 |
| WO | 2011160932 A1 | 12/2011 |
| WO | 2012130757 A1 | 10/2012 |
| WO | 2012159914 A1 | 11/2012 |
| WO | 2012160047 A2 | 11/2012 |
| WO | 2012160052 A1 | 11/2012 |
| WO | 2012161685 A1 | 11/2012 |
| WO | 2012162305 A1 | 11/2012 |

(56) References Cited

FOREIGN PATENT DOCUMENTS

| WO | 2013110601 A1 | 8/2013 |
|---|---|---|
| WO | 2013152861 A1 | 10/2013 |
| WO | 2013152894 A1 | 10/2013 |
| WO | 2015018901 A1 | 2/2015 |
| WO | 2015018903 A1 | 2/2015 |
| WO | 2015018904 A1 | 2/2015 |
| WO | 2015169431 A2 | 11/2015 |
| WO | 2015169732 A1 | 11/2015 |
| ZA | 9901520 A | 12/1999 |

OTHER PUBLICATIONS

"Activate". Collins English Dictionary, London: Collins, 2000, 2 pages. [Retrieved at http://search.credoreference.com/content/entry/hcengdict/activate/0 on Jun. 12, 2014].
"Lung Cancer". Merck Manual Home Edition, pp. 1-7. [Accessed at www.merck.com/mmhe/print/sec04/ch057/ch057a.html, on Jul. 28, 2010].
Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English of DE10007591, 2000.
Abstract in English of DE202006017793, 2007.
Abstract in English of FR2604363, Sep. 30, 1986.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226,1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Ackermann et al.; Quantitative Online Detection of Low-Concentrated Drugs via a SERS Microfluidic System; ChemPhysChem; 2007; vol. 8; No. 18; pp. 2665-2670.
Beasley R et al: "Preservatives in Nebulizer solutions: Risks without Benefit" Pharmacotherapy, Boston, US, Bd. 18, Nr. 1, Jan. 1998.
Beasley R et al: "Preservatives in Nebulizer solutions: Risks without Benefit" Pharmacotherapy, Boston, US, Bd. 18, Nr. 1, Jan. 1998, pp. 130-139.
Bocci et al., "Pulmonary catabolism of interferons: alveolar absorption of 125I-labeled human interferon alpha is accompanied by partial loss of biological activity". Antiviral Research, vol. 4, 1984, pp. 211-220.
Chen, F-K et al., "A study of forming pressure in the tube-hydroforming process". Journal of Materials Processing Technology, 192-193, 2007, p. 404-409.
China Suppliers, Shanghai Lite Chemical Technology Co., Ltd. Product details on polyvinylpyrrolidones. Obtained online by the USPTO examiner on Apr. 24, 2011.

Cras et al., "Comparison of chemical cleaning methods of glass in preparation for silanization". Biosensors & Bioelectronics, vol. 14, 1999, pp. 683-688.
Diamond et al., "Substance P Fails to Mimic Vagally Mediated Nonadrenergic Bronchodilation". Peptides, vol. 3, 1982, pp. 27-29.
Elwenspoek et al., "Silicon Micromachining", Chapter 3, Mechanical Microsensors, Springer-Verlag Berlin Heidelberg, 2001, 4 pages.
English Language Abstract of EP1068906, 2001.
Fuchs et al., "Neopterin, biochemistry and clinical use as a marker for cellular immune reactions". International Archives of Allergy and Immunology, vol. 101, No. 1, 1993, pp. 1-6, Abstract 1p.
Han et al.; Surface activation of thin silicon oxides by wet cleaning and silanization; Thin Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.
Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.
Ip et al., "Stability of Recombinant Consensus Interferon to Air-Jet and Ultrasonic Nebulization". Journal of Pharmaceutical Sciences, vol. 84, No. 10, Oct. 1995, pp. 1210-1214.
Jendle et al., "Intrapulmonary administration of insulin to healthy volunteers". Journal of Internal Medicine, vol. 240, 1996, pp. 93-98.
JP2005144459—English language abstract only.
Kutchoukov et al., "Fabrication of nanofluidic devices using glass-to-glass anodic bonding" Sensors and Actuators A, vol. 114, 2004, pp. 521-527.
Lougheed et al., "Insulin Aggregation in Artificial Delivery Systems". Diabetologia, vol. 19, 1980, pp. 1-9.
Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).
Niven et al., "Some Factors Associated with the Ultrasonic Nebulization of Proteins". Pharmaceutical Research, vol. 12, No. 1, 1995, pp. 53-59.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.
Trasch et al., "Performance data of refloquant Glucose in the Evaluation of Reflotron". Clinical Chemistry, vol. 30, 1984, p. 969 (abstract only).
Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.
Wang et al.; Self-Assembled Silane Monolayers: Fabrication with Nanoscale Uniformity; Langmuir; 2005; vol. 21; No. 5; pp. 1848-1857.
Abstract in English for WO2009050978, 2009.

* cited by examiner

MEDICINAL DEVICE WITH CONTAINER

The present invention relates to devices for administering liquid medicinal formulations, the fluidic connection of these devices to, for example, propellant-free containers which contain the liquid in question, and the outward sealing of the containers and the fluidic connection between the container and the device. In particular, the invention relates to smaller portable devices such as, for example, hand-operated nebulisers or injectors of the kind used for the inhalation or injection of liquid medicament formulations.

A large number of medical devices and nebulisers that are operated with a liquid are known from the prior art. In most of them, the liquid is placed in storage vessels or containers which contain several units of the liquid which is to be administered using the device. For removing the liquid or the units in the form of measured quantities from the container, a fluidic connection is provided between the device and the container, that is either permanent or capable of being interrupted, depending on the particular application. The fluid connection is created either by means of removal lines such as cannulas or tubes inserted in the container, or by the exposing of openings in the container and the connection thereof to associated channels within the device. This latter group also includes systems such as, for example, the metered dose inhalers (MDIs) containing propellant gas, in which a preliminary chamber or metering chamber is integrated in the container and the preliminary chamber is connected either to the liquid store or to the device by means of a switching mechanism, e.g. in the form of a movable pusher with corresponding guides.

What is common to all these systems is the need to outwardly seal the connecting point between the container and the device, whether it is static or dynamically moved, so that no liquid can escape from the system except through the prescribed expulsion route. The demands made of the sealing of the connection between the device and the containers depend, particularly in hand-held devices such as nebulisers, on the medicament formulation that is to be administered and its concentration, on the solvent used or on the climatic conditions at the place of use and can thus vary considerably. The interface between the container and the device must be tightly sealed and materially resistant to all substances from the medicament formulation. The formulation may contain not only liquid and solid constituents but also gaseous components, with a gastight seal generally imposing higher demands than a liquidtight seal. Some medicament formulations contain highly volatile substances such as, for example, ethanol which is often used as a solvent. When a volatile substance escapes separately from the container the concentration of the formulation may change. As a result, depending on the composition of the formulation, the concentration of an active substance in the solution may be increased or a dissolved substance may crystallise out. Such substances escape primarily in gaseous form: these substances, which by their nature have an increased vapour pressure, are rapidly partially converted into the gaseous phase, even inside the container, particularly when there are climatic changes. In some cases, even very small increases in temperature or drops in pressure in the environment of the container may lead to an increased gas formation in the container and this gas may partially escape through a seal which is primarily designed to be liquidtight.

A mechanical miniaturised high pressure nebuliser with which liquid medicament formulations for inhalation can be nebulised from a container holding a number of units of the formulation and inside which the liquid pathway is sealed off statically and dynamically is known from WO97/12687A1 and WO2009/047173A2. With this nebuliser, a liquid medicament formulation is conveyed from a rigid container with a collapsible inner bag inserted in the nebuliser, as disclosed in WO00/49988A2, out of the inner bag by means of a piston pump driven by a helical thrust gear and, by means of a spring-operated pressure pump, nebulised through a microstructured nozzle to form an inhalable aerosol. Details of possible microstructures for the expulsion nozzle inserted in the nebuliser are disclosed in the publications WO94/07607A1, WO99/16530A1, WO2005/000476A1 and WO2007/101557A2. WO2004/053362A1 describes a piston pump system that can be inserted in nebulisers of this kind, in which a predetermined amount of liquid is aspirated from the storage vessel into a pumping cylinder, by means of the axial movement of a hollow piston with non-return valve, and from there it is expelled through a liquid outlet. The hollow piston and chamber are sealed by an elastomeric O-ring seal in the guide tube of the hollow piston close to its entry into the pump cylinder; the geometric installation status of this seal is described more extensively in WO2007/051536A1.

WO00/49988A2 shows a liquid-filled cartridge closed off with a stopper, connected to the attachment part of a removal device or a nebuliser. The stopper comprises an immersion connector having a funnel-shaped centred guide for attaching a tubular removal connection belonging to the attachment part. The stopper forms a press fit with the inserted removal connector (see WO96/06011 A1 for variants of this stopper in the form of a closure cap for a container). The cartridge and attachment part are connected via a plug-in connection in which a plurality of snap-in hooks on the attachment part engage in an encircling groove in the upper part of the cartridge. Before being connected to the removal device, the cartridge or the upper open end of the immersion connector is sealed off with a sealing film, while the end of the immersion connector facing the inside of the cartridge is provided with a membrane which is pierced or folded open as the removal connector is inserted.

WO2006/087516A1 shows a sealing arrangement for attaching the valve stem of a pressurised container to a nebuliser or to a switching device for a nebuliser. This sealing arrangement comprises a first sealing portion which abuts directly on the outlet of the container, i.e. on the end face of the valve stem, and a second sealing portion at a spacing therefrom which seals off the side wall of the valve stem. The first sealing portion is a flat seal with a through-hole and the second is an O-ring seal. The two seals are redundant with respect to one another regarding their sealing function. The two are held together with a spacer by a solid cap and thus form a multi-part sealing arrangement.

The problem on which the present invention is based is to provide a device which is an improvement on the prior art, particularly a hand-held device such as a nebuliser or injector, for administering medicinal formulations from a container, in which the junction between the container and device is sealed off in liquidtight and gastight manner in accordance with the formulation used. In particular, the sealing system should have no permeability with respect to the liquid and gaseous substances of the formulation or should not allow any diffusion leaks, particularly if the formulations contain substances with a high vapour pressure such as ethanol, for example. The device with a sealing system at the junction of the container and device is intended in particular to be suitable for supplying measured amounts of liquid. The devices equipped with these sealing systems should be as independent as possible from their subsequent use, i.e. particularly independent of climatic conditions and more especially independent of climatic fluctuations or the use or therapy which is individually determined for the user under the circumstances. Depending on the therapy, the number of actuations per day envisaged for the device may vary from one device to another depending on the active substance formulation and the dosage. Moreover, the device with sealing system should be suitable for mass production. In particular, the sealing system should be particularly inexpensive with regard to the number and type of components and should be suitable for reliable assembly by mass production without suffering damage.

SUMMARY OF THE INVENTION

This problem is solved according to the invention by a device for administering a liquid medicinal formulation contained in a container inserted in the device. The container is pushed onto a rigid tube within the device, the tube being connected to a holder which receives the container in the device, for example by clamping. The container has an insertion point at which there is a first seal in the form of a fitting seal between the container and a section of the rigid tube which serves for removing liquid from the container. Between the holder and the container is a second seal which seals off the space between the first seal, the container and the tube to prevent the escape of liquid and gases and/or the penetration of gases.

The second seal additionally seals off the fluidic connection between the device and container from the environment. The two successive seals prevent the unwanted escape of liquid and gas from the container and/or the penetration of gas into the container more satisfactorily than the first seal on its own.

Advantageous further features are described hereinafter and in detail with reference to the drawings.

One feature of the present invention is that the first seal is substantially leaktight against the liquid components of the medicinal formulation in the container and the second seal is essentially leaktight against gases. Thus the demands of the leaktightness of the system as a whole are divided into different requirements imposed on two separate seals. This has the advantage that the individual requirements can be specifically met without any obligation to use a single solution which may be expensive or technically complex or defective in some respects. In this way, for example, a first seal at the container end may be designed primarily to hold back the liquid located within the container while fully respecting the requirements of the material compatibilities of the liquid and sealing material. The requirement that the fluidic connection between the device and the container should be gastight can be specifically met by means of the second seal. This means, among other things, that for this second seal, which may also be referred to a gas phase seal, the material may be selected, for example, primarily from the point of view of its permeability to gas, without the materials used necessarily having to be chemically compatible with the liquid in the container. This is of particular relevance to systems in which the container holds substances that are highly volatile such as ethanol, for example. Highly volatile substances exhibit both a high diffusion through very fine channels as a result of their vapour pressure and also, with lasting fluidic contact, significant diffusion through a plurality of plastics materials.

A further feature of the present invention is that whereas the first seal is formed by a fitting seal or press-fit between the container—preferably a partial region of an insertion funnel integrated in a container cap—and the tube that serves for the removal of liquid, the second seal is formed by only an additional component or an additional sealing layer between the container or the container cap and the holder for the container in the device. The sealing layer, the material of which is preferably softer than that of the container cap and holder, may for example be applied by moulding on, either on the side of the holder facing the container, or on the inner edge of the insertion point on the container or in the upper part of the container cap. In particular, both seals, both the first and second, act by direct contact with the container cap.

A seal formed by an additional component is preferably mounted on the device. It consists only of an elastomeric component which is compressed by the container cap and the device when the container is docked. This seal on the device side may be a cap-like or cup-like or sleeve-like or cone-like shape with a through-opening for the tube or it may be an O-ring seal, flat seal or ring seal.

As an alternative to the use of an elastomeric seal, both seals may be formed by the direct contact of the container cap with hard components of the device. In particular, they may be formed by press-fits between the container cap and the rigid tube serving to form the fluidic connection between the container and device, on the one hand, and a holder forming the container receptacle on the device on the other hand.

This measure provides an additional sealing of the junction between the container and the device with no or only one additional component. This sealing system is inexpensive and suitable for mass production. The double seal additionally has the advantage that occasional leaks cannot affect the leaktightness of the system as a whole. Such leakiness may be caused by sporadically occurring unevenness on a hard surface belonging to the sealing system, such as for example the surface of the tube in the region of the press-fit with the container cap. A second seal catches any leaks occurring at the first. As a result, demands made of the production process and possibly production costs may be reduced in some cases.

The devices shown here for administering medicinal formulations are preferably hand-held devices such as nebulisers or injectors, by means of which liquids are nebulised or injected in predetermined volumes or defined amounts.

Besides pure liquids and solutions the term "liquid" additionally encompasses dispersions, suspensions, suslutions (mixtures of solutions and suspensions) or the like. The term "medicinal formulation" or "medicament formulation" in the present invention, in addition to medicaments, refers to therapeutic agents or the like, i.e. in particular any kind of agent for inhalation or other types of application to humans and animals.

The individual features of the present invention may be used independently of one another or combined with one another.

Further advantages, features, properties and aspects of the present invention will become apparent from the following description of preferred embodiments by reference to the drawings.

DETAILED DESCRIPTION OF THE INVENTION

Figure 1:
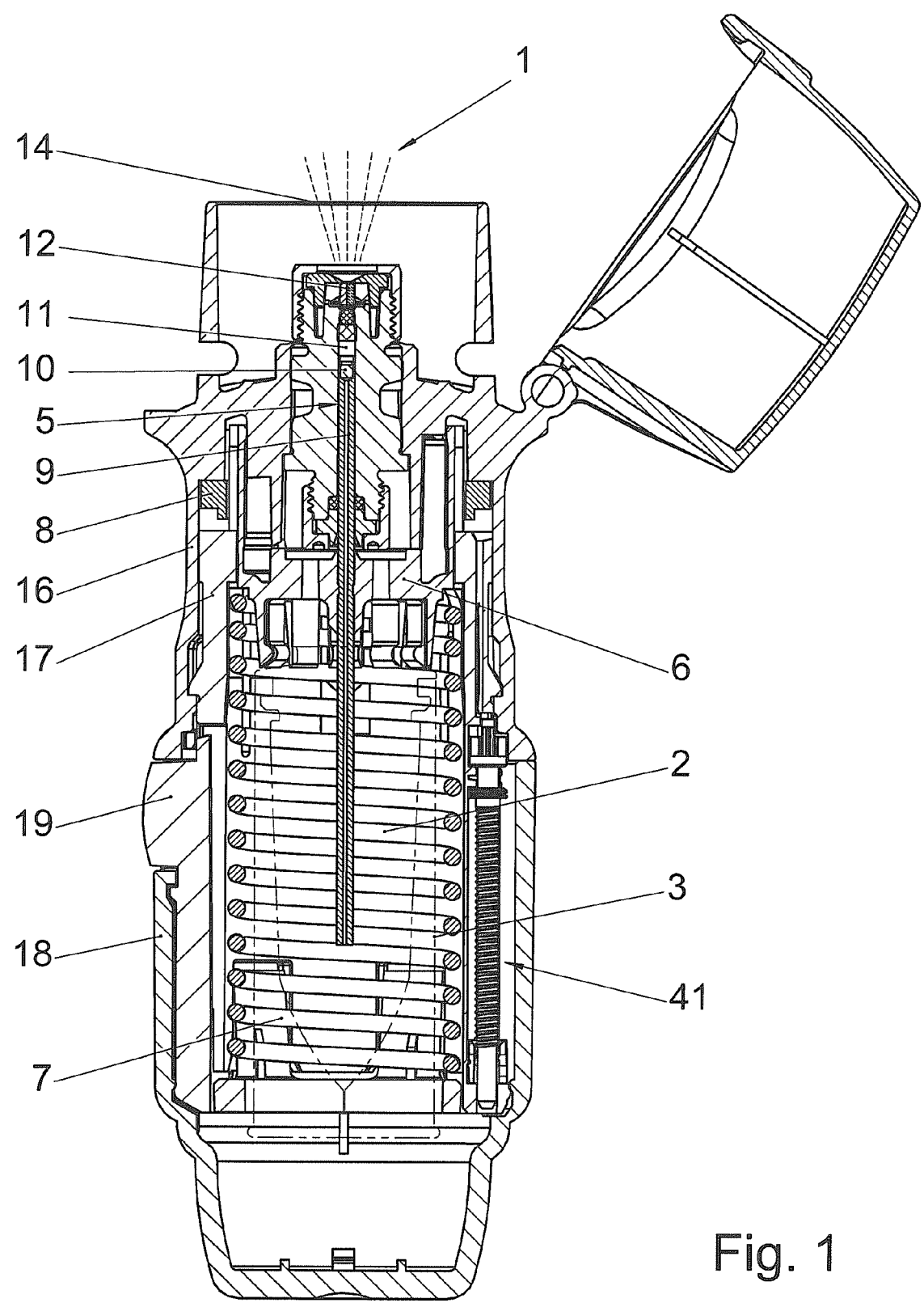
FIG. 1 shows a schematic longitudinal section through a nebuliser in the "untensioned" state.
Figure 2:
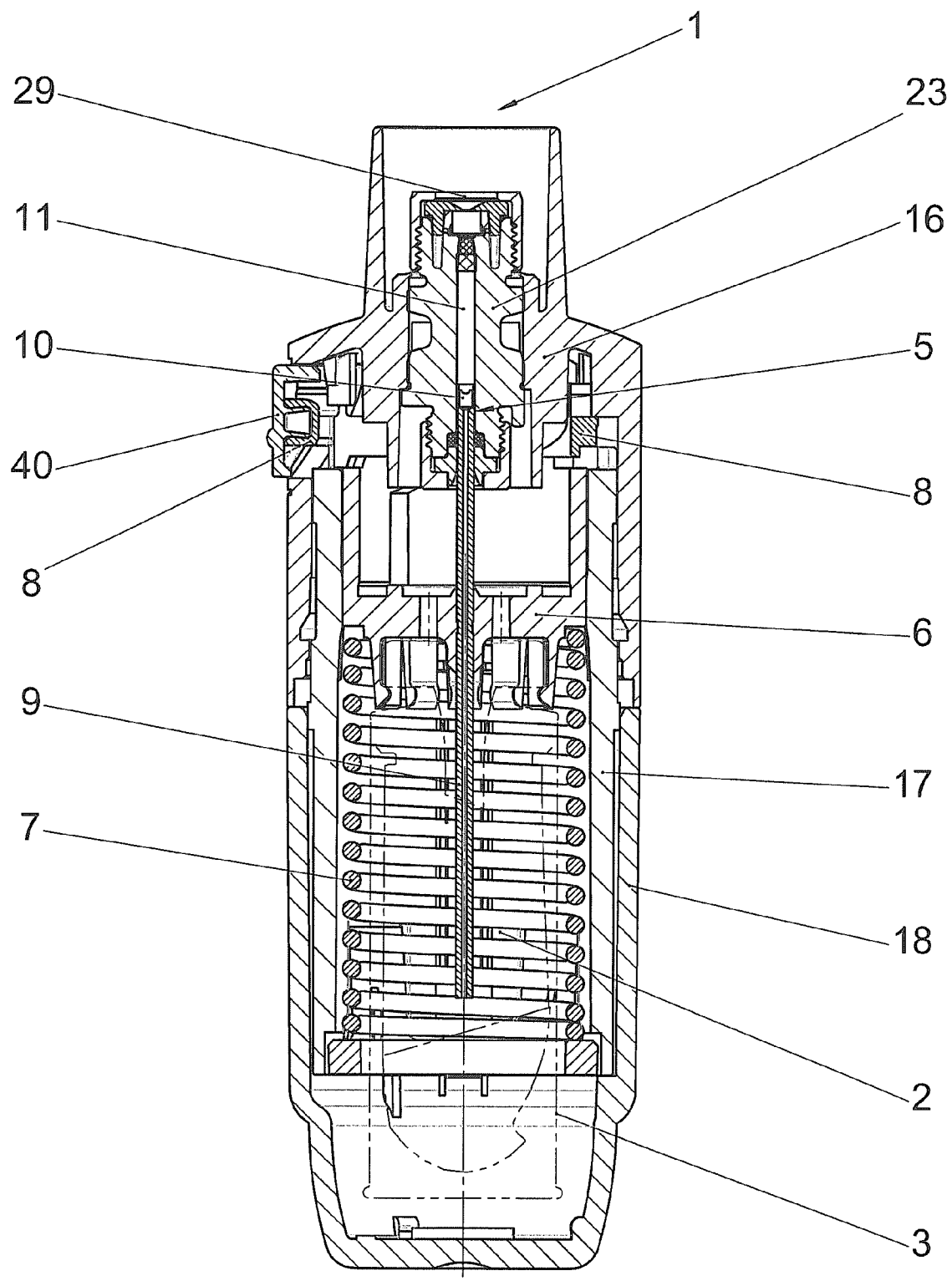
FIG. 2 shows a schematic longitudinal section through the nebuliser of FIG. 1, rotated through 90° compared with FIG. 1, in the "tensioned" state.

FIGS. 1 and 2 diagrammatically show a manually operated medical device in which the sealing system according to the invention can be used. The device shown in FIGS. 1 and 2 is a propellant-free nebuliser (1), which, on each actuating cycle, delivers the predetermined amount of a liquid (2) or a liquid medicinal formulation as a preferably lung-bound or inhalable aerosol (14) by means of a purely mechanical high pressure pump from the nozzle (12). This aerosol (14) with droplets having aerodynamic diameters of preferably 3-10 microns can be breathed in by a user (not shown). If the nozzle (12) of this device used for nebulisation is exchanged for the head of a liquid dispenser or an injection nozzle or a cannula or other injection device, all the operating principles independent of the nozzle remain unchanged. The correlations described hereinafter apply analogously to injectors or other liquid-delivery systems, even though only nebulisers are mentioned in the interests of simplicity.

In the operation of the nebuliser, a distinction is made between the so-called "untensioned" state with an unfilled metering volume in the pressure chamber (11) (FIG. 1) and the "tensioned" state with the pressure chamber (11) filled (FIG. 2). The terms "untensioned" and "tensioned" relate simultaneously to the state of the drive spring (7) incorporated in the nebuliser.

During the so-called "tensioning" of the nebuliser (1), its upper housing part (16) is rotated relative to the inner housing part (17) and lower housing (18) by a fixed rotation angle, e.g. 180°. A helical thrust gear mounted inside drives a piston pump by relative rotation, so that a predetermined, optionally adjustable amount of liquid (2) is conveyed from the container (3) into the pressure chamber (11) and at the same time the drive spring (7) acting on the hollow piston (9) is tensioned. The final state of the tensioning process is shown in FIG. 2. When the nebuliser (1) is actuated by the operation of the locking ring (8) using the button (40) the energy stored in the drive spring (7) is released. The hollow piston (9) previously used for delivering liquid, which is also part of the high pressure pump of the device, now presses into the pressure chamber (11) with its non-return valve (10) closed, so that the quantity of liquid predetermined by the lifting movement of the hollow piston (9) is expelled from there through the nozzle (12). The device is now in the released state again (FIG. 1).

Figure 3:
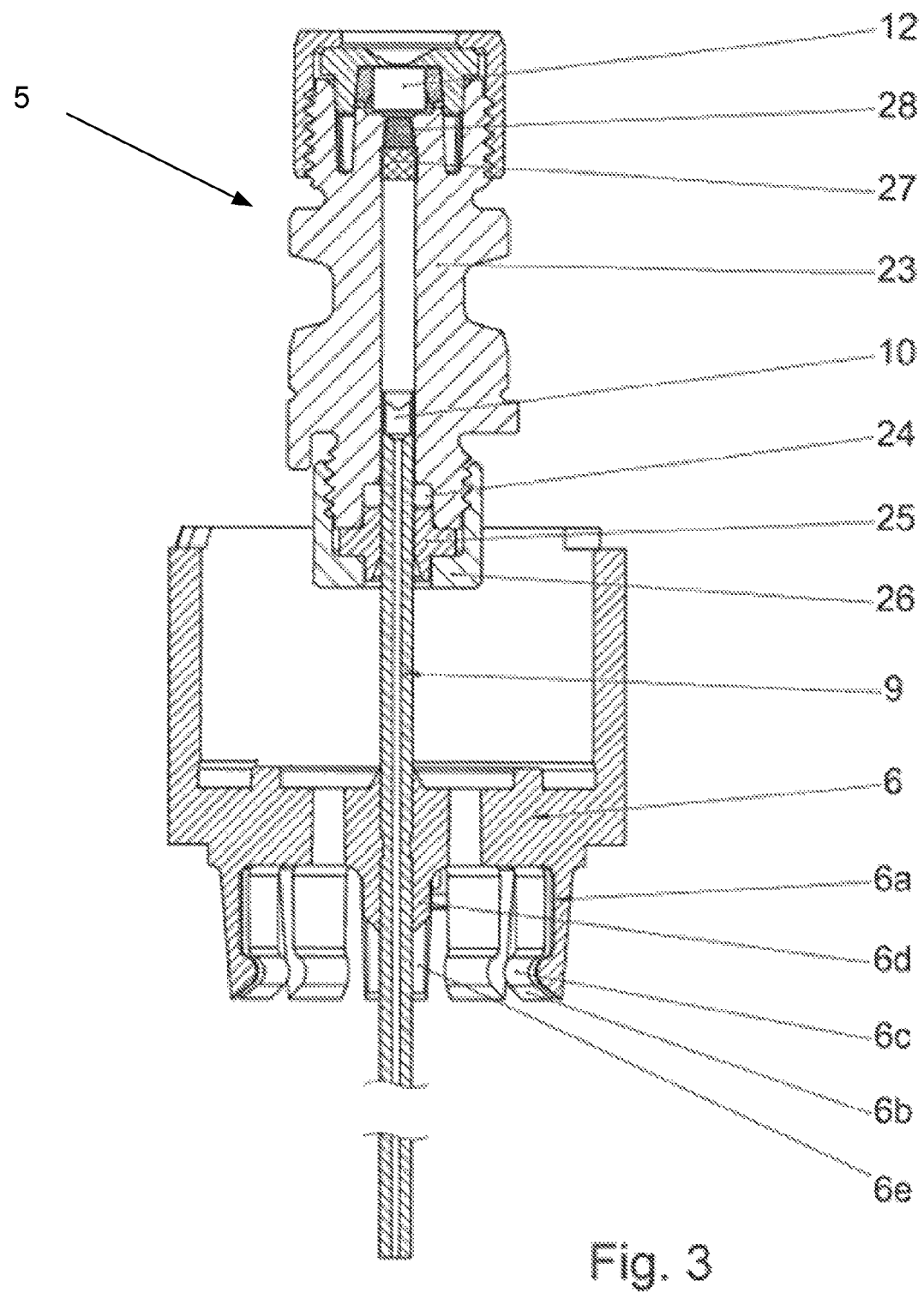
FIG. 3 shows a schematic longitudinal section through the nebuliser components of nozzle, filter, pump chamber, hollow piston and holder for the container (not shown).

FIG. 3 schematically shows the pressure generator (5) of the nebuliser (1) which, in the embodiment shown, is suitable both for nebulising aqueous liquid formulations and also, in particular, for nebulising formulations that contain a substance with a high vapour pressure or, more particularly, an alcohol compound, for example, as the solvent. The hollow piston (9) belonging to the piston pump system projects into the pressure chamber (11) on the container side. The hollow piston (9) is also the connecting element between the pressure chamber (11) and the interior of the container (3). The hollow piston (9) or a similar rigid tube or tubular component such as a capillary or cannula thus creates the fluidic connection between the device and container (3) when inserted in the container (3). If the hollow piston (9) is partly withdrawn from the pressure chamber (11) during the tensioning of the drive spring (7), a reduced pressure is produced by means of which liquid (2) is aspirated out of the container (3) into the pressure chamber (11) via the non-return valve (10) in the hollow piston (9), which is open in this position. If the hollow piston (9) moves into the pressure chamber (11) as the nebuliser (1) is actuated, the non-return valve (10) is closed by the abutment of its sealing surfaces on the seat in the hollow piston, and the liquid in the pressure chamber (11) is expelled under pressure through a filter system and the nozzle (12). The hollow piston (9) and pressure chamber (11) are sealed off to the outside by an elastomeric seal (24) which is, more particularly, in the form of an O-ring and is located in the guide tube of the piston close to its entry into the pressure chamber (11) or the metering chamber of the nebuliser (1). As this seal (24) seals off a space from a moving part—the hollow piston (9)—it may be referred to as a dynamic seal. Thus the high pressure pump is sealed off from the hollow piston (9) by a seal which is separate from the attachment of the hollow piston (9) to the container (3), more particularly a dynamic seal. In the embodiment shown the seal (24) is compressed by a support ring (25) which is held in position by a check nut (26). The geometric position of installation of the seal (24) corresponds, for example, to that described in WO2007/051536A1.

In the liquid outlet region of the pressure chamber (11) is a filter system (27, 28) which is located in front of the preferably microstructured nozzle (12) in the direction of flow and protects it from the depositing of particles. A high deposition rate is achieved by the combination of different kinds of filters (27, 28) and filtering techniques. In the case of the embodiment shown, the nozzle (12) is preferably formed by a microstructured component consisting of a glass-silicon composite which itself contains a very fine filter designed as a flow filter in front of the actual nozzle channel. The nebulisation of the liquid through these nozzle channels preferably depends on the high speed impact between two microscopic liquid streams from nozzle channels only a few microns in diameter.

The central part (23) forms the lateral limit of the pressure chamber (11), the liquid inlet in the form of the passage for the liquid-carrying hollow piston (9), the installation space for the seal (24) that seals off from the hollow piston (9), and the fluidic attachment to the nozzle assembly (29), which contains the nozzle (12) and various associated holder or sealing components. In the embodiment shown comprising a circular cylindrical pressure chamber (11), the central part (23) accommodates, in a central bore, one or more filter components attached to the pressure chamber (11). In the example shown, the filter components are a preliminary filter (27), preferably made of a plastic material, and a fine filter (28), preferably made of metal. Further downstream is connected the microstructured component described above which contains very fine filters and nozzle channels.

In the embodiment shown, the nebuliser (1) or its pressure generator (5) comprises a holder (6) for the container (3). This holder (6) is fixedly connected to the hollow piston (9), preferably moulded on, for example also adhesively bonded or snap-fitted. During the axial tensioning of the drive spring (7) the holder (6), together with the container (3) and the hollow piston (9), is moved downwards, in the drawings. The container (3) is fixed in the nebuliser (1) by means of the holder (6), particularly by a clamping or latching action, such that the hollow piston (9) projects into the fluid chamber of the container (3) and/or is fluidically connected to the liquid (2) in the container (3) and the liquid is aspirated through the hollow piston. The hollow piston (9) and container (3) are thus no longer moved relative to one another during the operation of the nebuliser (1) after the container (3) has been connected to the holder (6), i.e. after the container (3) has been docked on the device there is no relative movement of the components involved in sealing the junction between the device and container. The seals between the device and container (3) or container cap (31) are thus static. This has the advantage that the sealing system, by which the supply of liquid itself is protected from leaks and diffusions, is not subjected to any frictional stress whatever and therefore wear of the seals cannot take place. Preferably the container (3) and holder (6) form a plug-in connection in which, in particular, a plurality of snap-in hooks (6*a*) of the holder (6) engage in an encircling contour in the upper part of the container (3). This contour may be, for example, an encircling groove or, as in the embodiment shown, the lower collar edge of a container cap (31) that closes off the container (3). In the embodiments shown here, the holder comprises 4 to 12, preferably 6 or 12 snap-in hooks or ribs. If the container (3) together with its container cap (31) is pushed forwards along the hollow piston (9) into the holder (6), the container cap (31) first makes contact with the insertion slopes (6*b*) on the snap-in hooks (6*a*). The inwardly sloping insertion slopes (6*b*) cause the snap-in hooks (6*a*) to be spread outwards by the container cap (31) until the container cap (31) is able to slide past the inwardly directed beads (6*c*) of the snap-in hooks (6*a*). As soon as the lower outer edge of the container cap (31) has passed the bead (6*c*), the snap-in hooks (6*a*) spring back inwardly, so that the beads (6*c*) secure the container (3) at the lower edge of the container cap (31). If necessary, the holder (6) may be configured such that the container (3) is exchangeable. This exchangeability is achieved by means of the springy properties of the snap-in hooks (6*a*). The length, width and, above all, thickness and material of the holder (6) are selected accordingly. The holder (6) preferably consists of a plastic selected from among the thermoplasts such as, for example PPO (polyphenylene oxide) or PPE (polyphenylene ether) or PBT (polybutylene terephthalate). The geometry of the beads (6*c*) and the proportion of the beads (6*c*) on the inner circumferential circle of the holder (6) are matched to one another. For fine adjustment of the forces needed for the insertion or removal of the container (3) into or out of the holder (6) it is useful to equip only some of the ribs on the holder with beads (6*c*) to form snap-in hooks (6*a*). Thus, for example, the holder (6) in the embodiment shown in FIG. 3 has a total of three ribs without a bead (6*c*). These ribs without a bead (6*c*) serve merely for radial guidance of the container (3) inserted into the holder (6).

The exchangeability of the container is determined not only by the properties of the holder (6) but also by its accessibility: in the embodiment shown in FIGS. 1 and 2, a nebuliser is shown, the cap-like lower housing part (18) of which envelops the free end region of the container (3) inserted in the nebuliser. The lower housing part (18) is releasably attached by means of a retaining element or safety closure (19), and in particular is fitted onto the inner housing part (17). In particular, the retaining element or safety closure (19) is configured so as to prevent accidental opening of the nebuliser (1) or removal of the lower housing part (18). In order to release the lower housing part (18), in particular, the safety closure (19) has to be pressed in counter to spring force. The safety closure (19) is preferably a form that belongs to the inner housing part (17) and/or is moulded onto it, and configured in the form of a spring hook, for example.

Alternatively to the embodiment shown, the nebuliser (1) may also be configured such that the container (3) is pre-installed in the nebuliser. In this variant with a pre-installed container (3) (not illustrated in the drawings), the container (3) is inserted at the factory in the nebuliser (1) or in an additional retaining or securing element in the lower housing part (18) which is only partially pushed onto the inner housing part (17) when supplied. When it is pushed further onto the inner housing part (17) the lower housing part (18) slides, for example, over a ratchet pathway which is designed to slide only in one direction of movement or, after being pushed fully on, hooks permanently into a latching mechanism of variable configuration. At the same time, while the lower housing part is being pushed on, the container (3) is pushed into its holder (6) and connected to the hollow piston (9). Further details of the configuration of such systems with a pre-installed container (3) can be found in WO2006/125577A2.

Preferably, the medicinal devices under consideration here are designed for delivering a number of dosage units of the liquid medicinal formulation. Thus, the nebuliser (1) in FIG. 1 has a counter (41)—in this specific embodiment a spindle/cursor counter driven by the rotation of the housing, by means of which the user (not shown) can read off the quantity of dosage units taken or those remaining in the device. The container inserted in the device contains a quantity of liquid (2) which is sufficient for the removal of numerous—e.g. 30 to 180—dosage units. Because of this multiple delivery, the container (3) inserted in the nebuliser (1) must be such that the internal pressure remains substantially unchanged even when liquid is being removed, so that the same amount of liquid (2) is always removed on aspiration. This can basically be achieved using both a container (3) with a rigid container wall, the internal pressure of which is kept constant by means of a vent, as described for example in WO2006/136426A1, and also a container (3) with a flexible inner wall which moves at least partly into the interior of the container as liquid is withdrawn and thus keeps the internal pressure constant at the storage location for the liquid by reducing the internal volume. Containers (3) in which the flexible wall is formed by a bag (32) or inner bag or foil bag which is substantially deformable, compressible and/or collapsible are preferred. Containers of this kind are described in various embodiments in the publications WO00/49988A2, WO01/076849A1, WO99/43571A1, WO2009/11500A1 and WO2009/103510A1.

For the embodiments selected here, corresponding to which the attachment of the container is also shown in detail in FIGS. 4 to 9, a container is preferred in which the liquid (2) is located in a flexible, deformable and/or collapsible bag (32) or tube. In this way the internal pressure at the storage site of the liquid can be kept constant as liquid is withdrawn without any regular exchange of gases taking place with the environment of the nebuliser (1). Such an exchange of gas would have the disadvantage, particularly when using liquid medicinal formulations with highly volatile solvents such as ethanol, that a solvent fraction could escape through the gaseous phase in each venting process.

If solvent escapes through the gaseous phase, less solvent is left behind for the medicinal formulation in the container (3) and the active substance is concentrated in the liquid (2). As a result of this concentration, a relatively increased dose of active substance would be withdrawn when a measured quantity of liquid (2) was removed. Thus, this loss of solvent through the gaseous phase must be limited or if possible prevented. This is one of the demands made of the configuration of the container (3), the choice of materials used and the configuration of the seals when the container (3) is inserted in the respective device or in the nebuliser (1).

Preferably, a multilayered film or the like is used as the flexible wall material for the bag (32) that holds the liquid (2). The film comprises a plastics layer compatible with the medicinal liquid and a metal layer such as a layer of aluminium or the like. This minimises the diffusion or permeation of gas through the wall of the bag.

The container (3) selected for the embodiments shown comprises an inner bag (32), a flange (32a), a container cap (31) and a rigid sleeve (34). The flexible multilayer bag (32) which is closed at the bottom is directly connected at its upper part to a flange (32a), preferably made of plastics, that provides a grip. The rigid sleeve (34) surrounds the bag (32) and protects it outwardly from mechanical damage. The container cap (31) is preferably made of plastics, most preferably of HD-PE, and particularly a material that is the same as or similar to the flange (32a). After the bag (32) has been filled with liquid (2), the container cap (31) is tightly connected to the flange (32a) preferably by a thermo-forming process or a welding process (e.g. ultrasound or laser welding).

The container cap (31) comprises as the insertion point an insertion funnel (31a) projecting into the interior of the bag (32), which forms a centred guide for the hollow piston (9) when the container is attached to the nebuliser (1), and thus prevents the container (3) from being pierced by the hollow piston (9) in an uncontrolled manner with respect to the junction. Before being attached to the nebuliser (1) the container or the end of the insertion funnel (31a) facing the interior of the container (3) is closed off with a membrane (31b) which is pierced or flipped open when the hollow piston (9) is inserted. In this way, the membrane (31b) protects the un-pierced container from the escape of liquid. In addition, there is the possibility (not shown in the drawings) of providing the container during storage with a top seal which may consist for example, of a metal foil, preferably aluminium, and closes off the upper open end of the insertion funnel (31a). A seal of this kind may serve as a guarantee of origin and protect the insertion funnel (31a) from contamination during the transporting of individual cartridges. Gases that may possibly pass through the membrane (31b) are held back by a metallic top seal. Before the container (3) is installed in the device the top seal can be removed, e.g. by pulling it off using a protruding tab.

Figure 4:
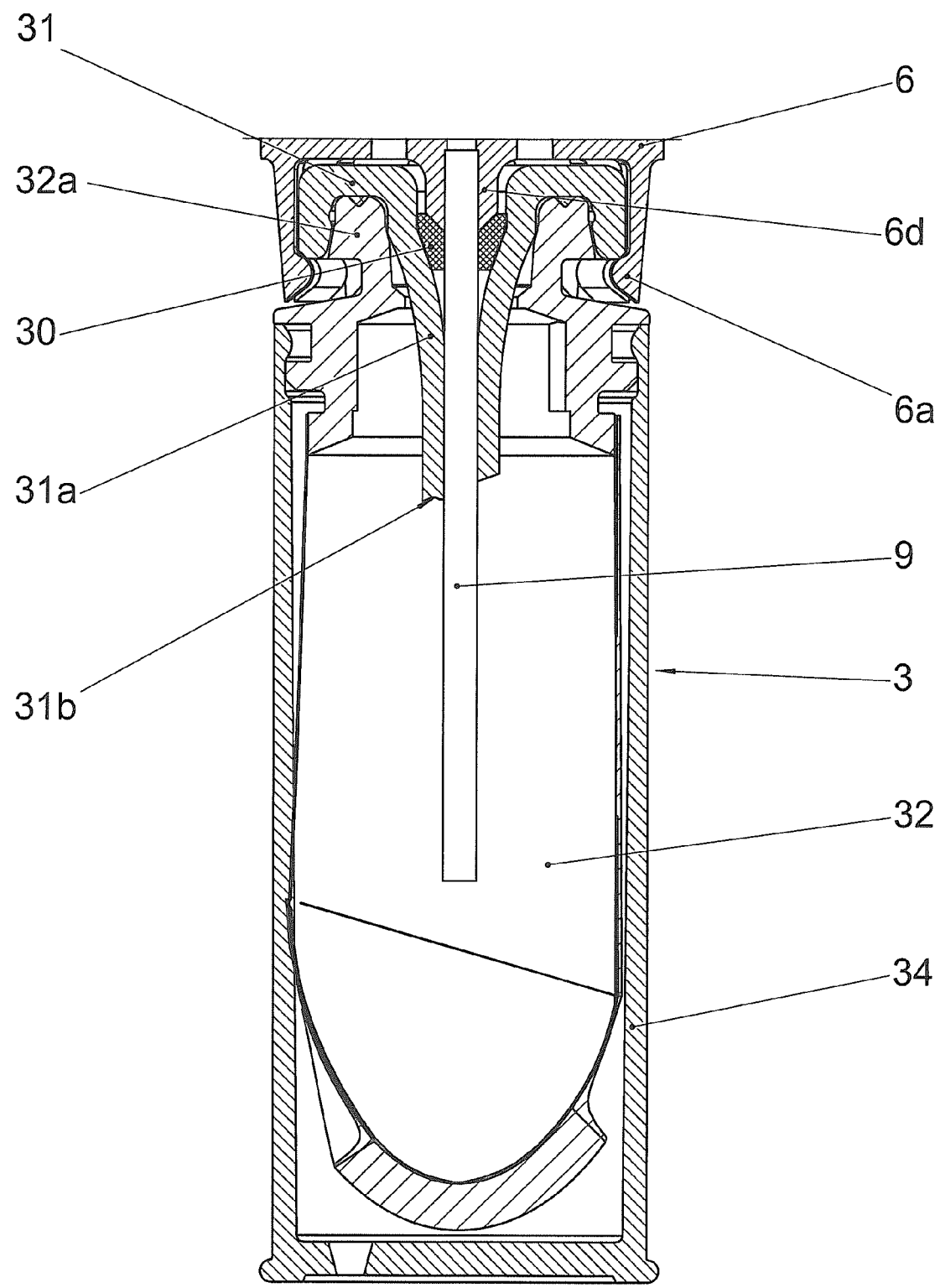
FIG. 4 shows a schematic longitudinal section through the point of attachment of a container to a delivery pump with a seal according to the invention
Figure 5:
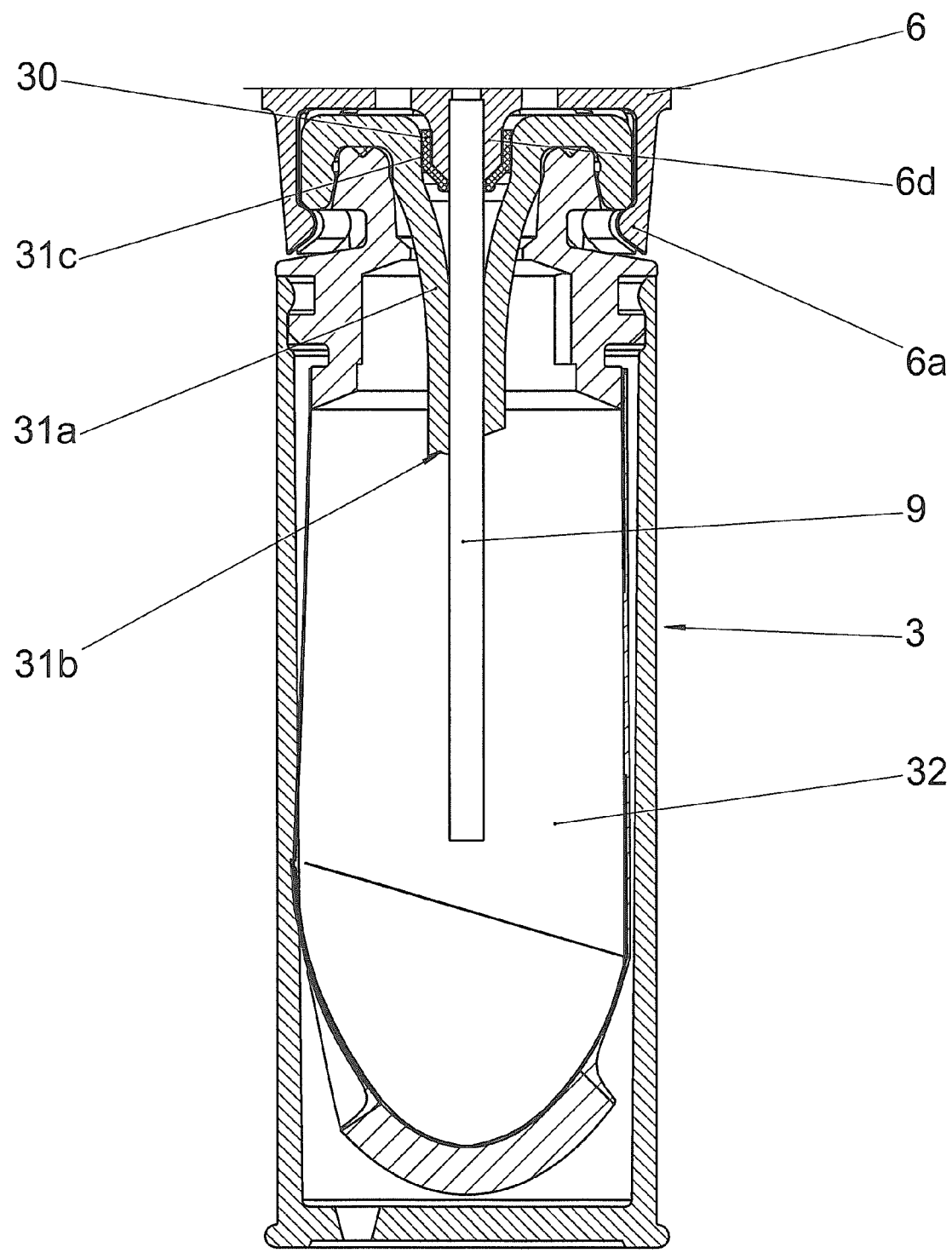
FIG. 5 shows a schematic longitudinal section through the point of attachment of a container to a delivery pump according to a second embodiment of the invention
Figure 6:
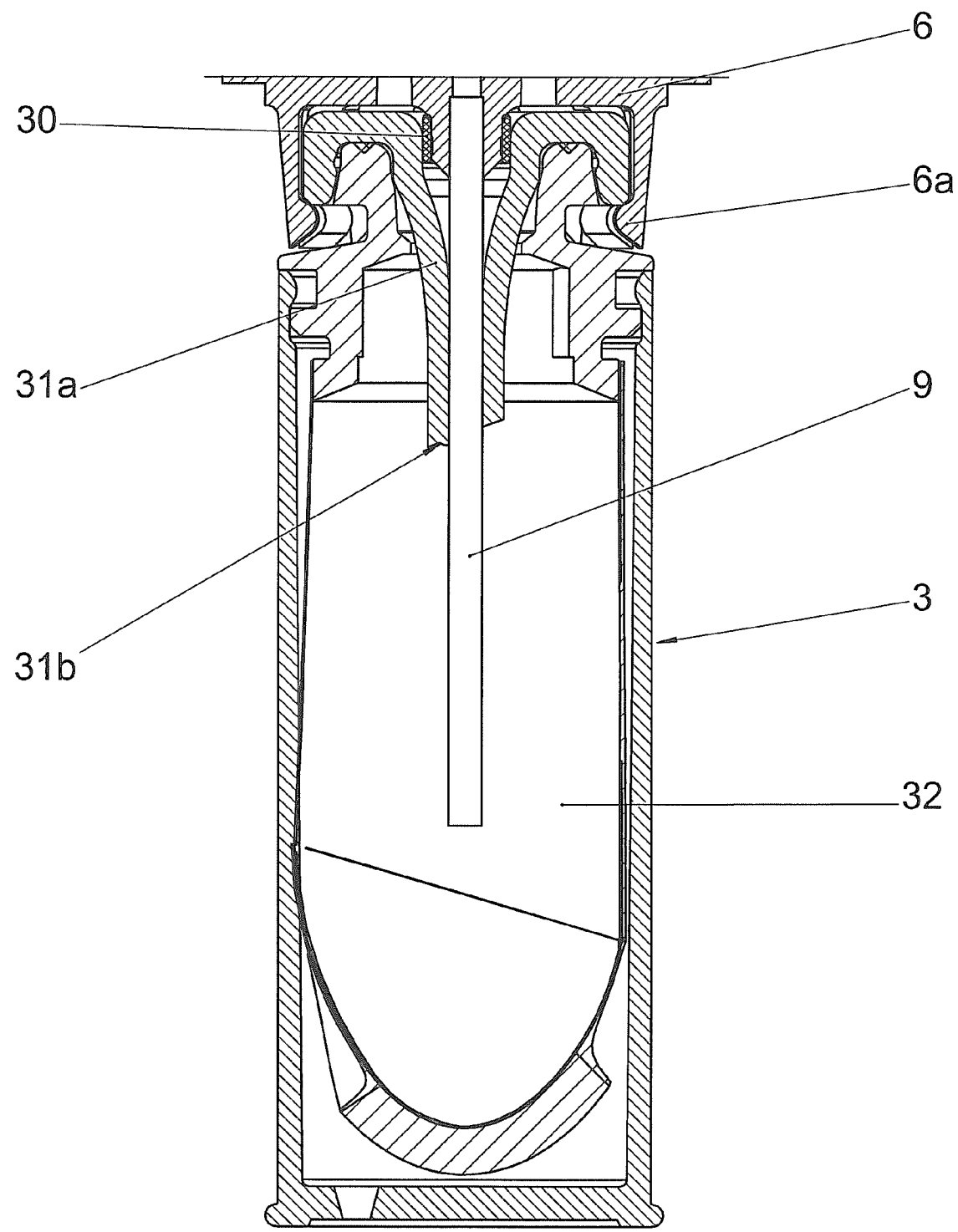
FIG. 6 shows a schematic longitudinal section through the point of attachment of a container to a delivery pump according to a third embodiment of the invention
Figure 7:
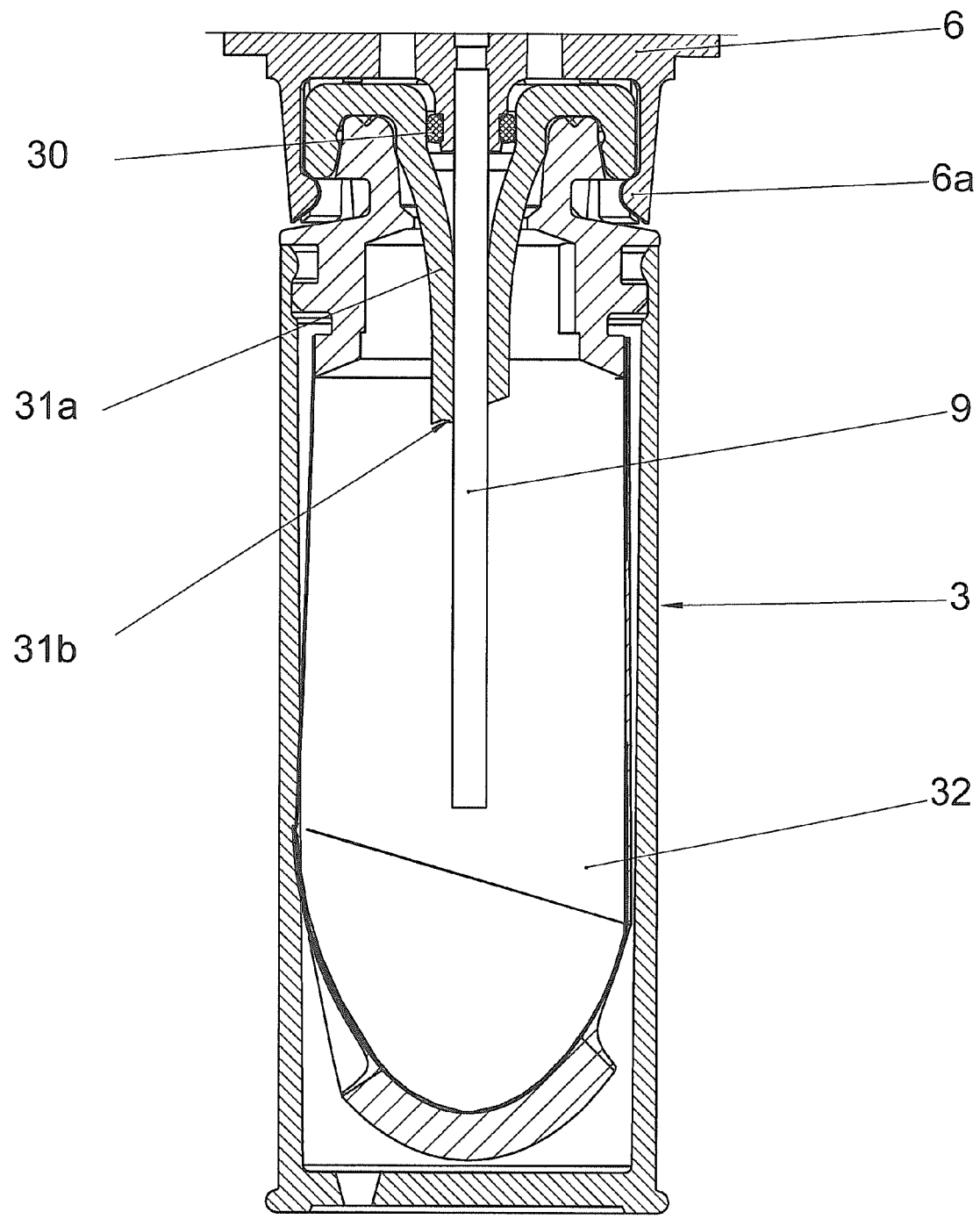
FIG. 7 shows a schematic longitudinal section through the point of attachment of a container to a delivery pump according to a fourth embodiment of the invention

After the container (3) has been fully inserted in the holder (6) of the nebuliser (1) there is a press-fit between the inserted tube or hollow piston (9) and the wall of the insertion funnel (31a). This press-fit in one part of the insertion funnel (31a) forms a seal belonging to the container cap (31), which is also referred to as the first seal. The radially acting press-fit seals the contact point between the hollow piston (9) and the interior of the container (3) against loss of liquid on the outside past the hollow piston (9) over a length of 1 to 10 millimeters, preferably 2 to 7 millimeteres, most preferably 5 mm. In the embodiment shown, the hollow piston (9) is made of metal, preferably stainless steel. The container cap (31) consists of a plastics material which is softer than the hollow piston (9), preferably PE or HD-PE. However, the material of the container cap (31) cannot be of unlimited softness as the inherent stability is important to the operational reliability of the system. For this reason, the press-fit between the hollow piston (9) and the insertion funnel (31a) may be designed to be sealed against the passage of liquid but not necessarily against permeability to gases. Depending on the method of manufacture of the hollow piston (9), there may for example be striations or uneven areas up to a few microns deep on its surface, which favour the permeation of gases through the press-fit. For this reason a second seal (30) with different sealing properties from the press-fit is installed at this point in order either to catch the gas escaping through the press-fit or in the approach area to prevent air entering the system from outside past the hollow piston (9). FIGS. 4 to 9 show different embodiments of the second seal (30). The holder (6) and hollow piston (9) are only shown in their lower part, in the interests of simplicity (a complete representation of these components can be found in FIGS. 1 to 3). FIG. 4 shows an example of the second seal (30) which is mounted as an additional sealing component on the outside of a tube such as the hollow piston (9) or on the holder (6) that forms the receptacle for the container and is provided on the device. A radially symmetrical seal (30) is shown here which seals off the container cap (31) and hollow piston (9) from one another in the upper part of the insertion funnel (31a), i.e. in its widened portion above the press-fit with the hollow piston (9). This second seal (30), which is located on the device side compared with the first seal, surrounds the hollow piston (9) radially in the region of the holder (6)—either directly or at a spacing produced by the inner guide (6d). The seal (30) here abuts with its upper side on the holder (6), particularly on the inner guide (6d), which is pulled downwards a little way along the hollow piston (9) towards the container (3). The seal (30) embodied as a component has on the inside a circular cylindrical recess for guiding the hollow piston (9), in the upper part a configuration which is funnel shaped in this embodiment and adapted to the shape of the inner guide (6d) of the holder (6) and on the outside a conical configuration tapering towards the container (3). This conical configuration forms a counterpart to the inner contour of the insertion funnel (31a) of the container cap (31). The seal (30), guided by the holder (6) with the hollow piston (9), projects into the conical opening which is provided in the container (3) or container cap (31) for the insertion of the hollow piston (9). In the installed position, the second seal (30) provides a seal in the conical wall portion of the insertion funnel (31a) of the container cap (31).

Preferably the seal (30) is pre-assembled on the holder (6), surrounding the hollow piston (9) and supported by the inner guide (6d). If the container (3) is then inserted in the nebuliser (1) and pushed axially onto the hollow piston (9), the seal (30) is axially compressed between the inner guide (6d) and the inner wall of the insertion funnel (31a) on the container cap (31). Looking at the attachment of the container (3) to the device as a whole, a sealing action is obtained by axial compression, particularly parallel to the tubular component or hollow piston (9) and by radial compression, particularly perpendicular to the hollow piston (9). By the combination of a radially acting seal in the form of the press-fit between the hollow piston (9) and container cap (31) and the essentially axially acting additional seal (30) between the container cap (31) and the container receptacle, the system is provided with a double-acting seal. The seal (30) preferably consists of an elastomer such as silicon and/or carbon-based elastomeric polymers. Suitable materials include natural and synthetic elastomers, for example nitrile rubber, butadiene rubber, styrene-butadiene rubber, isoprene rubber, styrene-isoprene copolymers, butyl rubber such as isobutene-isoprene rubber, polyurethane, fluorine rubber, siloxans such as in particular silicones and diene such as in particular EPDM (ethylene-propylene-diene rubber) or other elastomers suitable for use in the medical field. Depending on the requirements, e.g. the need for special material resistances or frictional properties related to the assembly process, the seal may additionally be coated. Thus, for example, sealing components coated with PTFE (polytetrafluoroethylene) consisting of fluorine rubber are advantageous against the background of improved separability on assembly machines for mass production.

The use of a soft elastomer, particularly one with a Shore hardness in the range from 40 to 70 Shore, for the seal (30) has the advantage that a hard-soft seal is formed both relative to the insertion funnel (31a) and relative to the hollow piston (9). Unevennesses in the comparatively hard surface of the insertion funnel (31a) and hollow piston (9) can thus be evened out by the seal (30), so that the transitional area between the components is also leaktight in respect of volatile substances. The seal (30) can thus also be termed a gas phase seal as the permeation of gases along the hollow piston (9) is prevented here. The seal (30) shown in the particular embodiment in FIG. 4 has the additional advantage that it projects into the insertion funnel (31a) and thus the dead volume, i.e. the unused free space between the second seal (30), the hollow piston (9) and the first seal (press-fit between the hollow piston (9) and container cap (31)) is kept comparatively small. The dead volume is constant as long as the container (3) is installed in the device. The components involved in the seal are not moved towards one another during the operation of the device or nebuliser (1). As a result of minimising the dead volume, equilibrium is rapidly established during the permeation of gas from the bag (32) through the press-fit, so that the total quantity of substances lost by the escape of gases can be kept very small. In the embodiment shown, the substance with the highest vapour pressure is usually the solvent of the medicinal formulation in the bag (32). The resulting minimising of the loss of solvent prevents concentration of the active substance in the solution. Tests have shown good long-term stability of the effect of the second seal (30). The gravimetrically determined evaporation values of containers (3) installed in devices using the seal (30) were just as low, depending on their material, as the unpierced containers (3) with an intact membrane (31b). With a total volume of the bag (32) of about 4 milliliters the evaporation values for ethanol in all the sealing materials tested and in all the individual samples were significantly below the threshold set for this experiment: the sealing system formed by the two seals between the container cap and device had an ethanol permeability of less than 0.3 milligrams per day. The results achieved were on average between 0.005 and 0.04 milligrams per day. Even when an elastomer such as silicon was used, which is known per se for its partial permeability for ethanol, the highest individual value measured was less than 0.15 milligrams per day.

FIG. 5 shows another embodiment of the second seal (30), embodied as a component, in the installed state. The material of the seal (30) corresponds to that used in the embodiment in FIG. 4. As in that embodiment, a material should be used for the special application which is, in particular, diffusion-proof to the substances contained in the medicinal formulation, i.e. does not allow any gas permeation of the solvent, for example. The component shown in FIG. 5 that forms the seal (30) is also radially symmetrical and is in the shape of a cup that has been opened at the bottom or a cap. The opening in the cup is the passage for the hollow piston (9). The inner shape of the sealing component or the inner contour of the cup is the counterpart to the shape of the inner guide (6d) of the holder (6) in the region of the hollow piston (9). In the particular embodiment, the sealing component has an upper circular cylindrical region which merges into a region that tapers conically downwards. The bottom of the cup is funnel shaped. Sealing is carried out by a purely radially acting compression of the seal (30) between the inner guide (6a) of the holder (6) and a circular cylindrical opening region (31c) of the container cap (31). This circular cylindrical opening region (31c) adjoins the insertion funnel (31a) in the upward direction on the container cap (31). Thus, in this embodiment, the two seals are formed by radial compression between the container (3) or container cap (31) and the hollow piston (9) or holder (6). The radial action of the seal (30) has the advantage that no additional axial forces have to be applied when inserting the container (3) in the device. The component forming the second seal (30) is shaped here so as to have a support region which in the axial direction abuts on another component of the device, particularly on the holder (6). The cap-shaped or cup-shaped configuration of the sealing component is adapted to the lower edge of the inner guide (6d) of the holder (6) and the inner base of the cup which forms the support region for the sealing component abuts at the bottom on the inner guide (6d). The support region of the component that forms the seal (30) thus abuts on the region of the holder (6) that projects into the container (3). Even if very soft sealing materials are used, the sealing component is held in position by this support and during docking, i.e. when the container (3) is inserted in the holder (6), it is not moved along by the axially acting forces in the upper axial space between the container cap (31) and the holder (6). In order to reduce the dead volume between the second seal (30), the container cap (31), the hollow piston (9) and the press-fit (first seal) the non-sealing supported lower region of the sealing component can be expanded. Preferably, this lower region of the component that forms the seal (30) has no direct wall contact with the insertion funnel (31a) of the container cap (31), so that during the docking of the container (3) no additional axial forces come into play.

FIGS. 6 and 7 show two further embodiments of the seal (30) in the installed state.

Analogously to the embodiment in FIG. 5, the seal acts radially between the inner guide (6d) of the holder (6) and the inner wall of the container cap (31), or specifically in the cylindrical opening region (31c) above the insertion funnel (31a). As a result of the radial action of the seal (30), no appreciable additional axial forces have to be applied when inserting the container (3) in the device. The seal is a hard-soft seal on both sides, in which the superficially soft material of the seal (30) evens out the surface unevenness of the container cap or of the inner guide (6*d*) of the holder (6) in the sealing region. The seal (30) may take the form of a flat ring seal which is fitted over the inner guide (6*d*) of the holder (6) (FIG. 6), or it may be in the shape of a flat or O-ring-shaped seal (30) set into the inner guide (6*d*) (FIG. 7) which is held in position by a radial depression on the inner guide (6*d*). Moreover, the inner guide itself may converge conically downwards and the seal (30)—adapted to the shape of the inner guide—may be a ring that expands downwardly and inwardly, which is inwardly supported on the inner guide (6*d*) (a variant not shown in the drawings).

A preferred assembly process for the seal (30) according to the embodiments in FIGS. 4 to 7 is as follows:

First of all, the hollow piston (9) is fixedly connected to the holder (6), preferably by moulding the plastic material of the holder (6) to the hollow piston (9) directly in an inlay injection moulding process. Then the holder (6) with the hollow piston (9) is mounted in the nebuliser (1) which is open on the container side (i.e. at the bottom in this case) but otherwise fully assembled. Before or preferably after the assembly of the holder (6) in the nebuliser (1) the radially symmetrical component that forms the seal (30) is pushed along the hollow piston (9) from below, in a centred manner, into its position on the holder (6) or on the inner guide (6*d*). This process is preferably carried out without any contact so as not to cause any damage to the hollow piston such as, for example, striations or other unevenness which could weaken the effectiveness of the first seal, in this embodiment the seal produced by the press-fit between the hollow piston (9) and the container cap (31). For contact-free assembly, a material with an elongation at break of at least 200%, preferably with an elongation at break of between 300% and 500% is used for the seal (30). In this context, this means that the radially symmetrical component can be expanded in diameter to at least double, preferably three to five times its size without any cracks forming. The material must also be selected so that the component undergoes purely elastic deformation during this loading and then returns to its original shape. The assembly of the component that forms the seal (30) is preferably carried out by means of a device in which at least three gripper arms project into the circular passage in the component and spread it out from the inside outwards. The spread-out component is pushed over the hollow piston (9) into its position on the holder (6). A plastic sleeve located on the inside between the grippers may additionally serve to protect the hollow piston. As soon as the component that forms the seal (30) has reached its axial position on the hollow piston (9) or holder (6), an outer sleeve is advanced which pushes the component downwards from the gripper arms as they are retracted. Depending on the shape of the sealing component or on the presence of a support region, a further fine adjustment of the position of the component that forms the seal (30) may also take place while the container (3) is being docked on the nebuliser (1) if the container cap (31), the seal (30) and the holder (6) are optionally pushed axially further together. After the assembly of the component that forms the seal (30) in the pre-assembled nebuliser (1), before delivery the latter may be closed off with a lower housing part (18) without a container, if desired, or preferably completed with a partially docked container (3) and lower housing part (18) to form a pre-assembled system.

Figure 8:
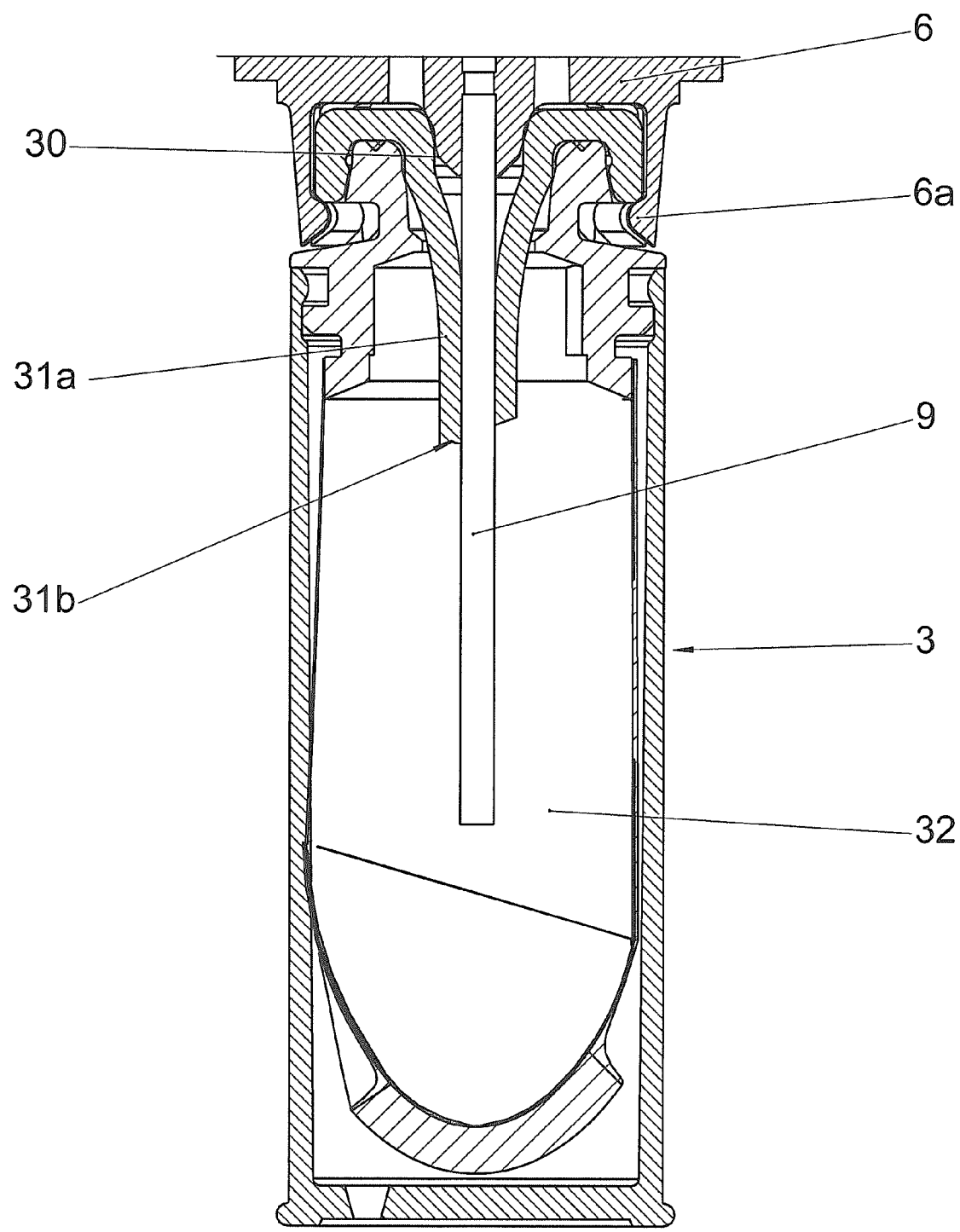
FIG. 8 shows a schematic longitudinal section through the point of attachment of a container to a delivery pump according to a fifth embodiment of the invention

FIG. 8 shows another embodiment of the second seal (30) in which the sealing action is achieved by the fit of the holder (6) and container cap (31). The holder (6) or its inner guide (6*d*) is shaped so that it forms the seal (30) itself by abutting directly on the container cap (31). This is particularly advantageous in terms of production costs and assembly methods as the seal (30) can be formed without the installation of an additional component. The holder (6) encloses the hollow piston (9) along a central portion and is permanently attached thereto, particularly by moulding on. The inner guide (6*d*) abutting on the hollow piston is significantly narrower by comparison with the total diameter of the holder (6) in all the embodiments and after the attachment of the container (3) to the holder (6) it projects into said container. The lower edge of the inner guide (6*d*) is then located lower than the upper edge of the container (3). The inner guide projects somewhat into the insertion funnel (31*a*) of the container cap (31).

Depending on the choice of materials in the alternative shown in FIG. 8, this second seal (30) is a hard-hard seal since, due to the requirement for retaining properties in the holder (6) and container cap (31), in particular, both components have to have a certain rigidity. For the container cap (31) a superficially softer material may indeed be used than is used for the holder (6) in this context, but the container cap (31) must have a certain rigidity. In the embodiment shown the inner guide (6*d*) is configured so as to abut on the container cap (31) in the upper opening region. Analogously to the example in FIGS. 6 and 7 it may form the seal in the cylindrical opening region (31*c*) or, as shown in FIG. 8, it may form the seal in the entry region of the cylindrical opening region (31*c*), i.e. in the surface region that is rounded during manufacture on which the top end of the container cap (31) merges into the circular cylindrical opening region (31*c*). In another embodiment which is not shown in the drawings, the inner guide (6*d*) may also abut directly in the upper region of the insertion funnel (31*a*). In this case, it preferably forms an encircling pointed edge which presses into the surface of the insertion funnel (31*a*), i.e. into the inwardly convergent slope, to form a better seal. This edge comes to a point preferably not only in the radial direction but also in the axial direction, i.e. the outer lower edge of the inner guide (6*d*) projects further in the direction of the container (3) then the material contact between the inner guide (6*d*) and the hollow pistons (9) formed by the moulding of material. In the region of the hollow piston (9) the inner guide (6*d*) thus comprises an undercut in this embodiment that is not shown. These seals (30) formed by the inner guide (6*d*) preferably act axially, so that, as in the embodiment shown in FIG. 4, they form a suitable combination for the radially acting, sealing press fit between the hollow piston (9) and container cap (31).

Figure 9:
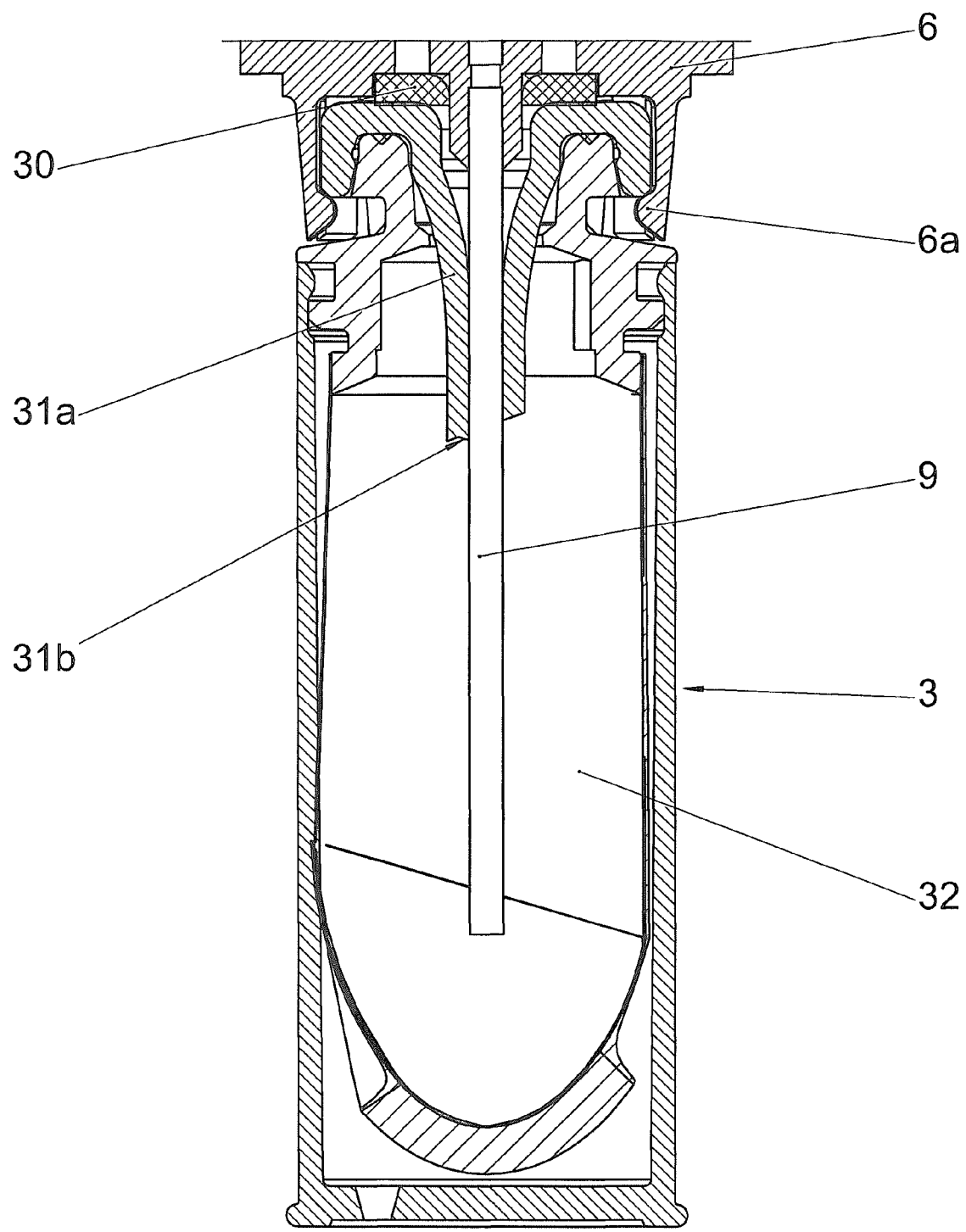
FIG. 9 shows a schematic longitudinal section through the point of attachment of a container to a delivery pump according to a sixth embodiment of the invention In the figures, the same reference numerals are used for the same or similar parts, where corresponding or comparable properties and advantages are obtained even if there is no repetition of the associated description.

FIG. 9 shows another embodiment of the second seal (30) in the installed position. The seal (30) is recessed or inset in the holder (6), as an independent component at the top end of the container. The seal (30) is in the form of a radially symmetrical flat seal, preferably a flat ring seal, which is optionally provided with internal insertion slopes. The material of the seal (30) corresponds to that in the embodiment in FIG. 4. The seal (30), by its compression, acts predominantly axially (parallel to the tube or hollow piston (9)), and thus forms a suitable combination for the radially acting, sealing press fit between the hollow piston (9) and the container cap (31). The seal is formed during the compression between the holder (6) and top edge of the container cap (31) as the container (3) is docked in the holder (6). On the inside, the component that forms the seal (30) abuts on the inner guide (6*d*).

Alternatively to the embodiments shown in the drawings, the second seal may also be formed by a sealing layer—a region that is additionally moulded onto the holder (6), the material of which differs from that of the holder (6). This additional material region may consist of an elastomeric material and may fill similar regions on the holder (6) to the independent elastomeric components in the embodiments according to FIGS. 9 and 4-7. The material is softer than that of the container cap and holder. This sealing layer may be formed from one of the above-mentioned elastomeric materials but particularly from a thermoplastic elastomer (TPE) such as, for example, one based on urethane or olefins. The sealing points and the action of the seal correspond to those in the embodiments in FIGS. 9 and 4-7, depending on the moulding-on region selected. Thus, where the previous embodiments mention a seal (30) which is "mounted" on the device, this expression includes, in addition to the individual components mounted on the device, sealing layers of the kind that are integrally connected to other components of the device.

Alternatively, the sealing layer may also be a region consisting of one of the elastomeric materials mentioned, which is additionally moulded onto the container (3) or onto the container cap (31). In this case, the sealing layer is located either on the inner edge of the insertion point or on the inner wall of the insertion funnel (31a) or in the upper region of the container cap (31). The sealing layer may be configured for example as one or more moulded-on tabs protruding upwards before the insertion of the container (3) into the holder (6) and then pressed inwards into the gap between the container cap (31) and the inner guide (6d) as the contours of the holder (6) are inserted. A sealing layer mounted on the container cap (31) in this way has the advantage, particularly in reusable devices, i.e. a nebuliser (1) which is operated with numerous containers (3) one after the other, that each seal (30) is used only once and cannot therefore be damaged in advance. Each container (3) introduces into the device a new unused sealing system consisting of a first and second seal.

In another embodiment (not shown) in which the second seal (30) acts similarly to the embodiment in FIG. 8, the holder (6) comprises an additional material region which is harder than the material of the container cap (31). For example, this additional material region may be an insert in multi-component injection moulding. This insert, preferably made of hard metal, could press into the material of the container cap (31) in the insertion funnel (31a) axially better at the lower end of the inner guide (6d) or—in the case of a single pairing of device and container—could cut in better than the plastic used for the moulding of the hollow piston (9) for the holder (6), which has to have a certain elasticity with regard to the nature of the snap-in hooks (6a).

The propellant-free nebuliser shown here serves to deliver a liquid medicinal formulation as an inhalable aerosol and is suitable for delivering both aqueous and also, preferably, alcoholic, particularly ethanolic, medicinal formulations. In particular, a liquid medicinal formulation which is to be administered and which contains a substance with a high vapour pressure or an alcohol compound is used here.

Preferred ingredients of the preferably liquid medicinal formulation are listed in particular in the publications WO09/047173A2 and WO09/115200A1, in which the lists of substances and formulation recipes given (WO09/115200A1, pages 25 to 40 and WO09/047173A2, pages 15 to 21) are incorporated by reference in their entirety. In particular, the fluids described in these publications may be aqueous or non-aqueous solutions, mixtures, formulations with and without solvent, such as ethanol or the like.

The proposal to equip the junction of a container with a device for delivering liquid with a dual seal against the loss of liquid and gas can be applied to numerous devices in which liquids are conveyed or transported. In particular, the invention is directed to all kinds of dosage withdrawal means, i.e. devices from which a predefined quantity of liquid is drawn from a container on each actuation. Moreover, the proposed nebuliser (1) operates mechanically, although the sealing system envisaged here is not restricted to use in purely mechanical devices for delivering a liquid. It may, for example, also be used in systems in which the liquid is delivered by electrical, hydraulic or other pumps or by propulsion means. Terms such as "pressure generator" should thus be understood in general terms. In this sense the present invention may also be used across different sectors; even applications beyond the medicinal or medical sector are possible.

| List of reference numerals | | | |
|---|---|---|---|
| 1 | nebuliser | 23 | central part |
| 2 | liquid | 24 | seal |
| 3 | container | 25 | support ring |
| 5 | pressure generator | 26 | check nut |
| 6 | holder (for container) | 27 | preliminary filter |
| 6a | snap-in hook (on holder) | 28 | fine filter |
| 6b | inner guide (on holder) | 29 | nozzle assembly |
| 7 | drive spring | 30 | seal |
| 8 | locking ring | 31 | container cap |
| 9 | hollow piston | 31a | insertion nozzle (in container cap) |
| 10 | non-return valve | | |
| 11 | pressure chamber | 31b | membrane (in container cap) |
| 12 | nozzle | 31c | cylindrical opening region (in container cap) |
| 12a | nozzle channels | | |
| 12b | very fine filter | 32 | bag |
| 14 | aerosol | 32a | flange (on the bag) |
| 16 | upper housing part | 34 | sleeve |
| 17 | inner housing part | 40 | button |
| 18 | lower housing part | 41 | counter |
| 19 | safety closure | | |

The invention claimed is:

1. A device for administering a liquid medicinal formulation, comprising:
   a container (3) having a flange (32a) defining an opening into the container (3) and an insertion point into the container (3);
   an insertion funnel (31a) having a first end at the flange (32a) and extending to a second end through the opening and into an internal volume of the container (3) that contains the liquid medicinal formulation, the insertion funnel defining a conically shaped inside surface of wider diameter at the first end than at the second end;
   a holder (6) configured to engage the flange of the container (3) and including a centrally located protrusion that extends into the first end of the insertion funnel (31a);
   a rigid tube (9) connected to the holder (6);
   a first seal in the form of a fitting seal located between the inside surface of the insertion funnel (31a), away from the first end and nearer to the second end, and a portion of the rigid tube (9); and
   a second seal (30) having elastomeric properties, and a through-opening through which the rigid tube (9) extends in an axial direction, the second seal (30) being located between the inside surface of the insertion funnel (31a), toward the first end thereof, and another portion of the rigid tube (9), where the second seal is located between the inside surface of the insertion funnel (31a) and the protrusion of the holder (6) such that contact by the protrusion of the holder (6) into the insertion funnel (31a) and biasing against the second seal (30) in the axial direction causes the second seal (30) to elastically deform in a radial direction and seal off a space between the first seal, the container (3) and the rigid tube (9) to prevent the escape of liquids and gases and/or to prevent the ingress of gases, wherein: the second seal (3) includes a first surface that engages against the inside surface of the insertion funnel (31a), the first surface is of a conical shape, the second seal (3) includes a second surface that is engaged by the protrusion of the holder, and the second surface is of a concave conical shape, the first seal includes a first area of contact between the inside surface of the insertion funnel (31a) and a first length of the portion of the rigid tube (9) that extends axially along the rigid tube (9), the second seal includes a second area of contact: (i) between the inside surface of the insertion funnel (31a) and an outside surface of the second seal, and (ii) between an inside surface of the second seal and a second length of the another portion of the rigid tube (9) that extends axially along the rigid tube (9), the first area of contact of the first seal and the second area of contact of the second seal (30) are axially displaced from one another along the rigid tube (9) such that a third length of the rigid tube (9) between the first and second lengths thereof forms no seal, and the third length of the rigid tube (9) is about a same length as an axial length of the second seal (30) extending along the tube (9).

2. The device according to claim 1 characterised in that the first seal is substantially leaktight against the liquid components of the medicinal formulation in the container (3) and the second seal (30) is substantially leaktight against gases.

3. The device according to claim 1, characterised in that the second seal (30) radially surrounds the rigid tube (9).

4. The device according to claim 1, characterised in that the second seal (30) is mounted at the device end on the tube or on the holder (6) that forms a container receptacle for the container (3).

5. The device according to claim 1, characterised in that the second seal (30) is axially compressed by the protrusion.

6. The device according to claim 1, characterised in that the second seal (30) is radially compressed perpendicularly to the rigid tube or perpendicularly to an inner guide (6d) on the holder (6).

7. The device according to claim 1, characterised in that the insertion point on the container (3) is facilitated by the insertion funnel (31a).

8. The device according to claim 1, characterised in that the second seal (30) is shaped so as to include a support region which abuts in the axial direction on the holder (6).

9. The device according to claim 1, characterised in that the holder (6) surrounds the tube and has an inner guide (6d) that is narrower by comparison with the holder's overall diameter and abuts on the tube, wherein the inner guide (6d) comprises a lower edge which is lower than the flange (32a) of the container (3) and projects somewhat into the insertion funnel (31a) when the container (3) has been inserted into the holder (6).

10. The device according to claim 1, characterised in that the rigid tube (9) is a hollow piston inserted in the container (3) or is a capillary or a cannula.

11. The device according to claim 1, characterised in that the rigid tube (9) forms a piston of a high pressure pump.

12. The device according to claim 1, characterised in that the liquid medicinal formulation that is to be administered contains a substance with a high vapour pressure or an alcoholic compound.

13. The device according to claim 1, characterised in that the second seal (30) is formed from a material that is softer than that of the holder (6).

14. The device according to claim 3, characterised in that the second seal (30) is spaced apart from the rigid tube (9) by an inner guide (6d) on the holder (6).

15. A device for administering a liquid medicinal formulation, comprising:

a container (3) having a flange (32a) defining an opening into the container (3) and an insertion point into the container (3);

an insertion funnel (31a) having a first end at the flange (32a) and extending to a second end through the opening and into an internal volume of the container (3) that contains the liquid medicinal formulation, the insertion funnel defining a conically shaped inside surface of wider diameter at the first end than at the second end;

a holder (6) configured to engage the flange of the container (3) and including a centrally located protrusion that extends into the first end of the insertion funnel (31a);

a rigid tube (9) connected to the holder (6);

a first seal in the form of a fitting seal located between the inside surface of the insertion funnel (31a), away from the first end and nearer to the second end, and a portion of the rigid tube (9); and a second seal (30) having elastomeric properties, and a through-opening through which the rigid tube (9) extends in an axial direction, the second seal (30) being located between the inside surface of the insertion funnel (31a), toward the first end thereof, and another portion of the rigid tube (9), where the second seal is located between the inside surface of the insertion funnel (31a) and the protrusion of the holder (6) such that contact by the protrusion of the holder (6) into the insertion funnel (31a) and biasing against the second seal (30) in the axial direction causes the second seal (30) to elastically deform in a radial direction and seal off a space between the first seal, the container (3) and the rigid tube (9) to prevent the escape of liquids and gases and/or to prevent the ingress of gases, wherein:

the first seal includes a first area of contact between the inside surface of the insertion funnel (31a) and a first length of the portion of the rigid tube (9) that extends axially along the rigid tube (9);

the second seal includes a second area of contact: (i) between the inside surface of the insertion funnel (31a) and an outside surface of the second seal, and (ii) between an inside surface of the second seal and a second length of the another portion of the rigid tube (9) that extends axially along the rigid tube (9);

the first area of contact of the first seal and the second area of contact of the second seal (30) are axially displaced from one another along the rigid tube (9) such that a third length of the rigid tube (9) between the first and second lengths thereof forms no seal; and the third length of the rigid tube (9) is about a same length as an axial length of the second seal (30) extending along the tube (9).

\* \* \* \* \*